(12) United States Patent
Di Rago et al.

(10) Patent No.: US 8,143,061 B2
(45) Date of Patent: Mar. 27, 2012

(54) INDUSTRIAL METHOD FOR PRODUCING RNA AND SYSTEM FOR CARRYING OUT SAID METHOD

(75) Inventors: Jean-Paul Di Rago, Sainte Helene (FR); Nathalie Bonnefoy, Gif-sur-Yvette (FR); Stéphane Duvezin-Caubet, Bordeaux (FR)

(73) Assignees: Centre National de la Recherche Scientifique, Paris (FR); Universite Victor Segalen Bordeaux 2, Bordeaux (FR)

( * ) Notice: Subject to any disclaimer, the term of this patent is extended or adjusted under 35 U.S.C. 154(b) by 1148 days.

(21) Appl. No.: 10/564,512

(22) PCT Filed: Jul. 22, 2004

(86) PCT No.: PCT/FR2004/001957
§ 371 (c)(1),
(2), (4) Date: May 12, 2006

(87) PCT Pub. No.: WO2005/010194
PCT Pub. Date: Feb. 3, 2005

(65) Prior Publication Data
US 2007/0072272 A1 Mar. 29, 2007

(30) Foreign Application Priority Data
Jul. 23, 2003 (FR) ..................................... 03 09024

(51) Int. Cl.
C12N 15/74 (2006.01)
C12N 15/70 (2006.01)
C12P 19/34 (2006.01)

(52) U.S. Cl. .................. 435/483; 435/471; 435/91.1

(58) Field of Classification Search .................. None
See application file for complete search history.

(56) References Cited

U.S. PATENT DOCUMENTS 3,272,714 A 9/1966 Watanabe et al.
2009/0098653 A1* 4/2009 Koob et al. ............... 435/459

FOREIGN PATENT DOCUMENTS

EP 0 317 209 5/1989

OTHER PUBLICATIONS

Fox et al. Plasmids can stably transform yeast mitochondria lacking endogenous mtDNA. PNAS 85: 7288-7292, 1988.*
Lisowsky et al. A nuclear mutation affecting mitochondrial transcription in *Saccharomyces cerevisiae*. Eur. J. Biochem. 164: 559- 563, 1987.*
Dziembowski et al. The yeast mitochondrial degradosome. Its composition, interplay between RNA helicase and RNase activities and the role in mitochondrial RNA metabolism. J. Biol. Chem. 278(3): 1603-1611, 2003.*
Komiya et al. Recognition of mitochondria-targeting signals by a cytosolic import stimulation factor, MSF. J. Biol. Chem. 269(49): 30893-30897, 1994.*
Hwang et al. Expression of functional influenza virus RNA polymerase in the methylotrophic yeast *Pichia pastoris*. J. of Virology 74(9): 4074-4084, 2000.*
Finch. Transformation in Fungi. Micro. Rev. 53(1): 148-170, 1989.*
Kim et al. Overexpression of Bcl-X(L) inhibits Ara-C-induced mitochondrial loss of cytochrome c and other perturbations that activate the molecular cascade of apoptosis. Cancer Res. 57: 3115-3120, 1997.*
Di Rago et al. Molecular basis for resistance to antimycin and diuron, Q-cycle inhibitors acting at the Qi site in the mitochondrial ubiquinol-cytochrome c reductase in *Saccharomyces cerevisiae*. J. Biol. Chem. 263(25): 12564-12570, 1988.*
Kaisho et al. Increase in gene expression by respiratory-deficient mutation. Yeast 5: 91-98, 1989.*
Shahhosseini et al. Expression and secretion of an alpha-amylase gene froma native strain of *Bacillus lichenformis* in *Escherichia coli* by T7 promoter and putative signal peptide of the gene. J. Appl. Micro. 95: 1250-1254, 2003.*
Bonnefoy et al. In vivo analysis of mutated initiation codons in the mitochondrial COX2 gene of *Saccharomyces cerevisiae* fused to the reporter gene ARG8m reveals lack of downstream reinitiation. Mol Gen Genet. Jan. 2000;262(6):1036-46.*
Dekker et al. In-vitro translation of mitochondrial mRNAs by yeast mitochondrial ribosomes is hampered by the lack of start-codon recognition. Curr Genet. Jan. 1993;23(1):22-7.*
Anziano, Paul Q et al.: "Splicing-defective mutants of the yeast mitochondrial COXI gene can be corrected by transformation with a hybrid maturase gene", Proceedings of the National Academy of Sciences of USA, National Academy of Science. Washington, US, vol. 88, No. 13, pp. 5592-5596, Jul. 1991.
Bonnefoy, Nathalie et al.: "Genetic Transformation of *Saccharomyces cerevisiae* Mitochondria", Methods in Enzymology, Academic Press Inc, San Diego, CA, US, vol. 350, pp. 97-111, 2001.

* cited by examiner

Primary Examiner — Michele K Joike
(74) Attorney, Agent, or Firm — Oblon, Spivak, McClelland, Maier & Neustadt, L.L.P.

(57) ABSTRACT

The invention relates to an industrial method for producing an interest heterologous RNA and to a system for carrying out said production method consisting (1) in transforming mitochondrions of yeast cells free of mitochondrial RNA with a mitochondrial transcription vector comprising at least one copy of the DNA encoding said interest heterologous RNA which are controlled by regulatory element(s) of the mitochondrial transcription and a reporter gene thereof or a fragment of said reporter gene, 2) identifying yeast transformants by incorporating the interest DNA into the mitochondrions thereof, (3) culturing the yeast mitochondrial transformants selected at the stage (2), (4) isolating the mitochondrions from the yeast mitochondrial transformants obtainable at stages (3) and in extracting and purifying the interest heterologous RNA from said mitochondrions.

18 Claims, 4 Drawing Sheets

INDUSTRIAL METHOD FOR PRODUCING RNA AND SYSTEM FOR CARRYING OUT SAID METHOD

The present invention relates to an industrial method for producing RNA of interest.

The present invention also relates to a system for carrying out the industrial production of RNA of interest.

There exists in fact a need for the production of large amounts of RNA of interest for producing medicinal products (interfering RNA or siRNA), studying RNA structure (crystallization, NMR, complexes), and analyzing gene function in vitro in cell culture or in vivo, in particular by inhibition of the expression of these genes with siRNAs.

The methods normally used for producing a specific RNA sequence are essentially in vitro transcription and chemical synthesis.

In vitro transcription reactions use bacteriophage (SP6, T7 or T3) RNA polymerases. The yield from these synthesis reactions and the amounts of product obtained is in general limited, in particular because of limiting factors such as the nucleotide concentrations (inhibitory effect of nucleotide concentrations>8 mM, for example), the concentrations of the various elements constituting the reaction medium, and in particular the concentration of $Mg^{++}$ ions. In general, it is accepted that magnesium concentrations must be in excess in in vitro transcription reactions. The use of pyrophosphatase, in combination with $Mg^{++}$ ions, has also been proposed and is considered to improve the transcription reaction yield.

Another complication encountered in the in vitro synthesis of polynucleotides is the inhibition of the phage polymerases at relatively low ion concentrations.

In order to avoid these various drawbacks, the use of improved reaction media has been proposed in U.S. Pat. No. 5,256,555, which describes the use of a reaction medium comprising high total molar concentrations of nucleotides (between 12 mM and 40 mM) which were previously considered to be inhibitory concentrations, and an effective molar amount of $Mg^{++}$, which is below saturation with regard to the total molar concentrations of nucleotides, of pyrophosphatase and of $Mg^{++}$-nucleotides or tris-nucleotides.

Despite the various improvements proposed, in vitro transcription for producing RNAs of interest has the following drawbacks:

induction of parasitic reactions (N+1 activity) which increase the heterogeneity of the transcription products and require a thorough purification of the RNA;
limitation with regard to the amount and to the size of the RNA synthesized;
relatively high production costs.

Although cellular systems exist for producing proteins of interest in vivo, in particular in yeast cells, no comparable system exists for producing RNAs of interest.

Specifically:

American patent U.S. Pat. No. 3,272,714 relates to the industrial production of RNA from yeast cultured in a medium in which the concentration of zinc and of phosphoric acid and also the oxygen absorption coefficient are controlled; the method described does not make it possible to specifically produce an RNA of interest, but only a large amount of all the endogenous yeast RNAs (total yeast RNA);

European patent application 0 317 209 relates to the industrial production of heterologous proteins. To increase the level of expression of a heterologous gene of interest in yeast, it is recommended to replace the conventional yeast strains transformed with an expression vector for the gene of interest according to the standard protocols of cyto-plasmic transformation (lithium chloride), with respiration-deficient yeast strains obtained by deletion of all or part of the mitochondrial genome ($rho^0$ and $rho^-$ strains), transformed with this same vector. Said respiration-deficient transformed yeast are cultured in a medium containing a fermentable carbon source (glucose). Even if this system described for the production of proteins was transposed to the production of RNA, it would not make it possible to specifically produce an RNA of interest, but only a mixture of endogenous yeast RNAs and of exogenous RNAs of interest in which the proportion of RNA of interest in the total yeast RNA fraction is increased.

The applicant consequently gave itself the aim of providing a method for producing RNA which does not have the drawbacks of the methods normally used and which thus more successfully meets the practical needs, in that it makes it possible to synthesize in vivo, in a cellular system, any RNA of interest in large amounts or with a high yield and at a cost that is significantly lower than that obtained with the in vitro methods of the prior art.

Figure 1:
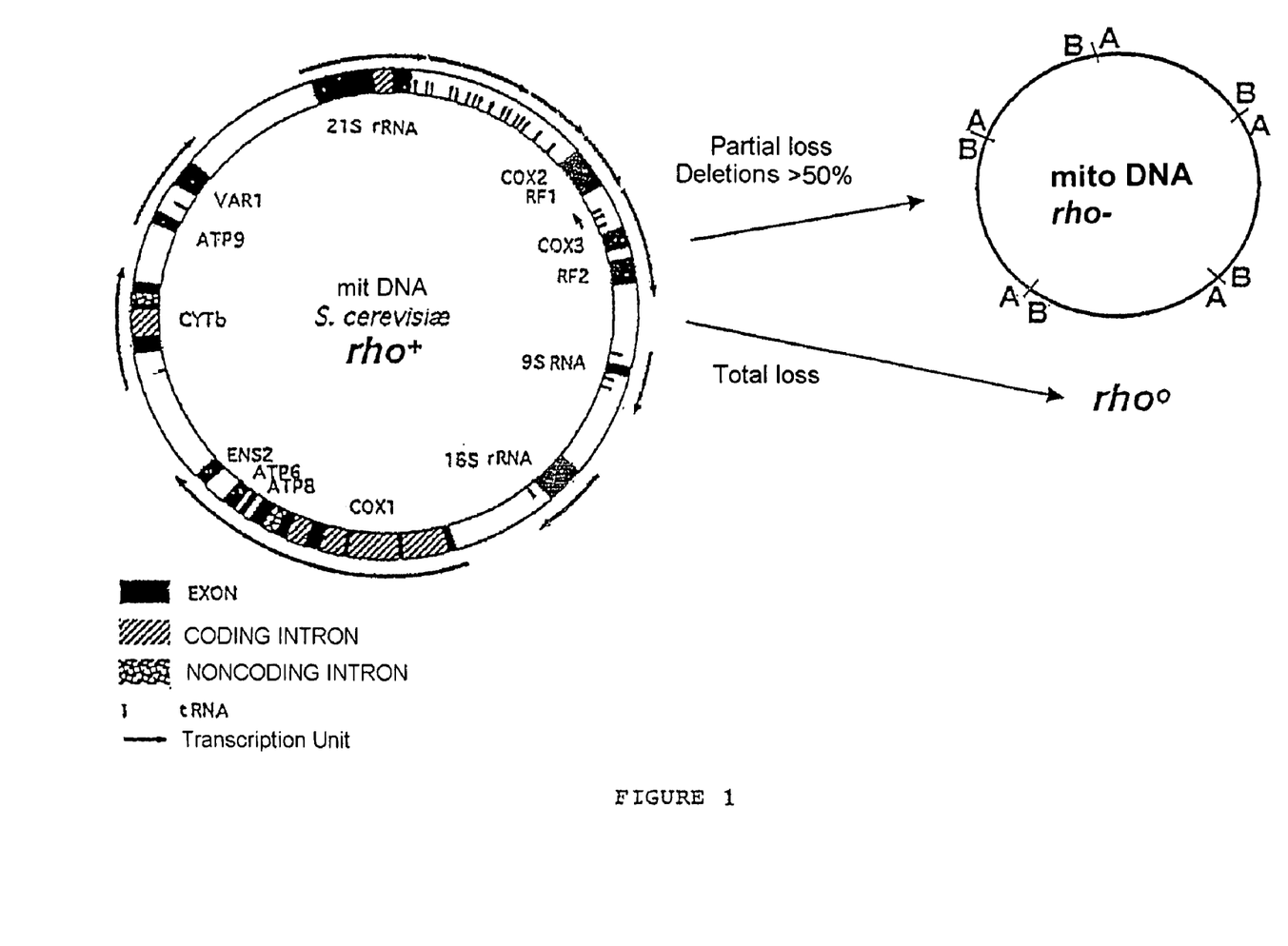
FIG. 1 illustrates the mitochondrial DNA of *S. cerevisiae*; the mitochondrial DNA encodes in particular: 3 subunits of ATP synthase (6, 8, 9); 4 subunits of the respiratory chain; 2 rRNAs+1 mitoribosome; 24 tRNAs.

Mitochondria are cell organelles that have their own genetic information; yeast mitochondrial DNA contains the genes of some proteins required for the respiratory function of mitochondria, and also some genes required for the functioning of the mitochondrial protein synthesis system (FIG. 1). Methods of mitochondrial transformation (biolistic bombardment method) have been developed in yeast, with the aim of analyzing mitochondrial gene function and regulation of their expression (Johnston et al., Science, 1988, 240, 1538; Bonnefoy et al., Methods in Enzymology, 2001, 350, 97, 111; Anziano and Butow, P.N.A.S., 1991, 88, 5592-5596). In a first step, a yeast strain lacking mitochondrial DNA ($rho^0$ strain) is bombarded with an exogenous DNA adsorbed onto metal microprojectiles, so as to produce a synthetic $rho^-$ strain; the exogenous DNA, generally a plasmid, contains all or part of the gene to be analyzed and a fragment of a marker or reporter (gene of the respiratory chain allowing growth in non-fermentable medium). In a second step, the synthetic $rho^-$ yeast that have incorporated the exogenous DNA are identified by crossing with $rho^+$ tester yeast comprising a mutation in said marker or reporter genes, and isolation of the synthetic $rho^-$ yeast able to produce diploids capable of growing in non-fermentable medium.

The synthetic $rho^-$ strain thus identified is crossed with a yeast strain suitable for studying said mitochondrial gene (strain carrying a mutation in said gene or wild-type strain (reverse genetics)) and the cis effect (homologous recombination) or trans effect of the mitochondrial gene is analyzed in the yeast resulting from the cross.

The applicants have shown that $rho^0$ yeast strains can advantageously be transformed with a DNA encoding a heterologous RNA of interest (RNA not encoded by a mitochondrial gene) and used for producing the RNA of interest in their mitochondria. This RNA is readily isolated in a stable form and in large amounts, from the mitochondria of the synthetic $rho^-$ strain, insofar as the only RNAs produced in the mitochondria of said synthetic $rho^-$ strain are those which are encoded by the DNA used for the transformation.

Consequently, a subject of the present invention is a method for producing a heterologous RNA of interest, which method is characterized in that it comprises at least the following steps:

(1) transforming the mitochondria of yeast cells, in particular *S. cerevisiae*, cells lacking mitochondrial DNA ($rho^0$ strain) with a mitochondrial transcription vector comprising the DNA encoding said heterologous RNA of interest under the control of regulatory element(s) for mitochondrial transcription, and a mitochondrial transformation reporter gene or a fragment of said reporter gene; the method according to the invention thus allows the transcription of any heterologous DNA sequence whatever its intraspecific or interspecific origin (including the mitochondrial DNAs of organisms other than yeast or chloroplast DNAs), and also synthetic DNA sequences that do not exist naturally; a mitochondrial transformant or a synthetic rho⁻ strain is thus obtained;

(2) identifying the yeast mitochondrial transformants that have incorporated the DNA of interest;

(3) culturing the yeast mitochondrial transformants selected in step (2), preferably in the exponential growth phase;

(4) isolating the mitochondria from the yeast mitochondrial transformants cultured according to step (3), and (5) extracting and purifying the heterologous RNA of interest from said mitochondria.

Under the conditions of the methods according to the invention, the RNA obtained is stable.

The method of the invention makes it possible to simultaneously produce one or more RNAs of interest from the mitochondrial transcription vector.

Figure 2:
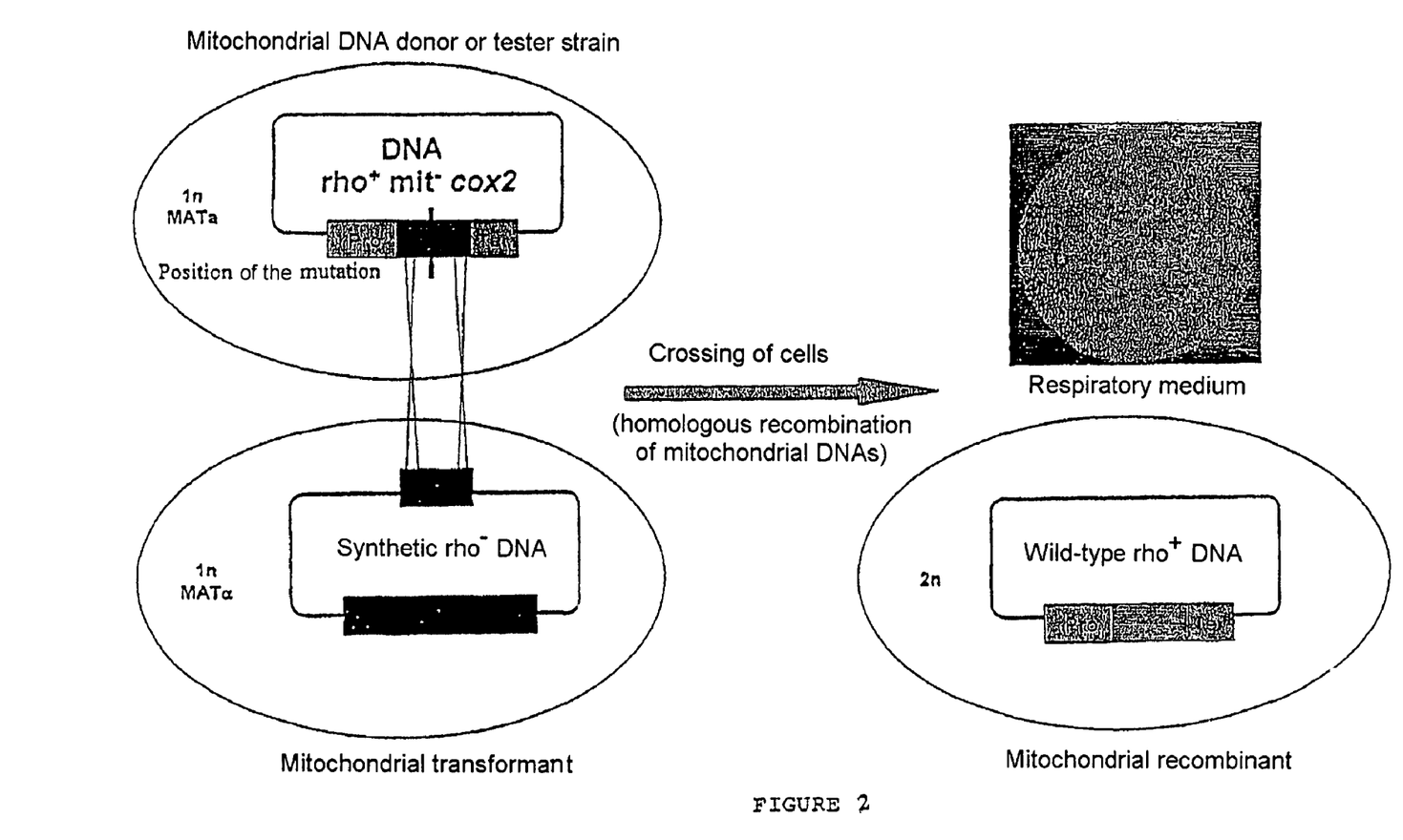
FIG. 2 illustrates the principle of marker rescue.
Figure 3:
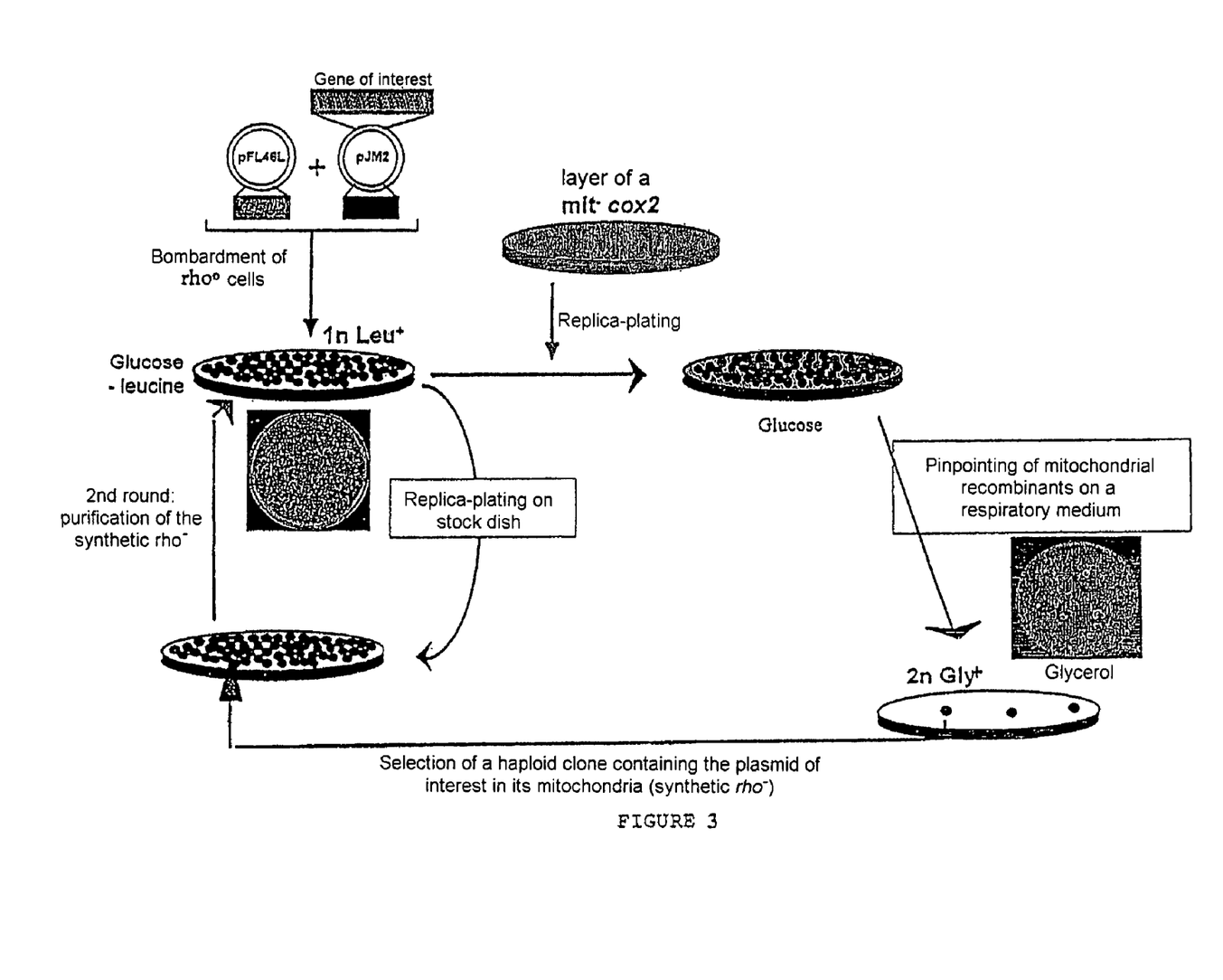
FIG. 3 represents the construction of a synthetic rho⁻ strain.

Definitions (see FIGS. 1 to 3)

the terms "yeast cell", "yeast strain", "cell", "yeast" and "strain" are considered to be equivalent in the context of the present invention and are used without distinction; the same is true for the rho⁺, rho⁰ and rho⁻ yeast strains as defined below.

Heterologous RNA of interest: any natural or synthetic RNA not encoded by the yeast mitochondrial genome.

rho⁺ Strain: yeast strain comprising an intact and functional mitochondrial DNA as in wild-type strains, or mitochondrial DNA carrying local alterations in its sequence, of mit– type, which inactivate the respiratory function of mitochondria (FIG. 1).

rho⁰ Strain: yeast strain lacking mitochondrial DNA, characterized by an inability to grow in a medium containing a non-fermentable carbon source and an absence of mitochondrial protein synthesis (FIG. 1).

rho⁻ Strain: yeast strain comprising a large deletion, always greater than 50%, of the mitochondrial genome. The conserved region of the mitochondrial genome is reiterated, directly or as a palindrome, so as to reconstitute a mass of mitochondrial DNA equivalent to that that exists in a wild-type yeast cell. The deletions of rho– type always entrain with them at least one of the mitochondrial genes required for mitochondrial protein synthesis, given that these genes are distributed uniformly along the mitochondrial genome. The rho⁻ strains are therefore phenotypically equivalent to rho⁰ strains with the loss of all mitochondrial protein synthesis activity and therefore total inactivation of the respiratory function of the organelle (FIG. 1).

Synthetic rho⁻ strain: yeast strain initially rho⁰, the mitochondria of which have been transformed with an exogenous DNA (heterologous DNA), in particular by the abovementioned method of biolistic bombardment of yeast cells. This transformation is made possible by the ability of the yeast cells to be able to replicate and maintain any DNA fragment, in particular a bacterial vector (plasmid). For the reasons listed above, no protein can be synthesized in the mitochondria of synthetic rho⁻ cells. On the other hand, the mitochondrial transcription machinery is functional in these cells. Thus, the introduction of a DNA fragment carrying a gene of interest under the control of mitochondrial transcription signal sequences, into mitochondria of an rho⁰ cell, makes it possible to obtain a yeast strain expressing, in its mitochondria, only the RNA of said gene but not the corresponding protein. As in a natural rho⁻ strain, the DNA introduced artificially into the mitochondria will be reiterated so as to produce in the organelle a mass of DNA equivalent to that present in mitochondria of an rho⁺ wild-type strain. The gene of interest will therefore be present in the synthetic rho⁻ strain at a relatively high copy number (more than 3000 for a gene of interest of approximately 1 kb). It is therefore for these properties similar to those of (natural) rho⁻ cells that such cells are called, by analogy, synthetic rho⁻ cells (FIG. 2).

mit⁻ Strain: yeast strain comprising a local alteration (nucleotide substitution, short deletion or insertion) in the sequence of a mitochondrial gene that encodes one of the subunits of the mitochondrial energy system, such as the COXII or COX2 gene.

Mitochondrial transformants: transformants obtained in particular by bombardment of yeast cells, according to the abovementioned biolistic method. The bombardment of an rho⁰ strain results in the production of mitochondrial transformants which are synthetic rho⁻ transformants. Any vector can be used for the bombardments, but for identifying the mitochondrial transformants, a vector comprising a marker for the yeast mitochondrial genome, for example the COX2 gene, or a fragment of said gene, is required.

Mitochondrial recombinants: they are obtained by homologous recombination after the synthetic rho⁻ strain has been brought into contact with an rho⁺ strain.

Auxotrophic marker: mutation in a known gene of the pathway for biosynthesis or use of an amino acid, of a nucleotide, of a carbon-based substrate, etc.

Surprisingly, the method according to the invention:

can be readily industrialized (use of conventional fermenters), and effectively makes it possible to obtain RNA of interest in large amounts, for a low cost, after a purification that can be readily set up.

In addition, it has the following advantages:

the fact that it includes an in vivo synthesis, in yeast, of the RNA of interest allows it to benefit from all the cellular quality controls, in particular: (1) maximum transcription fidelity, considerably minimizing the risks of error of incorporation, by several orders of magnitude compared with existing methods, and (2) an absence of post-transcriptional modifications which have the effect of changing the sequence of the RNA compared with the sequence of its gene, because there is no editing of the RNA in yeast mitochondria, the production costs are essentially independent of the length of the RNA. They consist essentially of the purchase of relatively inexpensive reagents (culture media and products for purifying the RNA), whereas the methods of the prior art use very expensive reagents (nucleotides, enzymatic kits) in large amounts.

Such a method therefore constitutes a particularly advantageous alternative to the methods for producing RNA in vitro, according to the prior art, economically and from the point of view of the quality of the molecules produced.

In accordance with the invention, prior to step (1), said DNA encoding the RNA of interest can be amplified, in particular by PCR, and it is then cloned into said mitochondrial transcription vector. In such a case, the oligonucleotide primers are established in the following way: the oligonucleotide P1 is complementary to the 5' region of the DNA of interest, adjacent to transcription +1. It advantageously comprises a restriction site for cloning the amplified DNA into the transformation vector and, optionally, a site that facilitates purification of the RNA of interest. The oligonucleotide P2 is, itself, complementary to the 3' region of the DNA of interest, adjacent to the transcription stop. Here also, the oligonucleotide advantageously comprises a restriction site for cloning the amplified DNA and, optionally, sequences that facilitate purification of the RNA of interest. The sequences that facilitate purification of the RNA of interest are in particular sequences complementary to oligonucleotides coupled to a solid phase; for example, an oligodA sequence makes it possible to purify the oligoA-RNA thus obtained, using an oligodT coupled in particular to magnetic beads. Advantageously, said sequences that facilitate purification of the RNA of interest are cleavable sequences.

According to an advantageous embodiment of said method, said DNA sequence encoding the RNA of interest is under the control of a promoter and of a transcriptional terminator that are functional in yeast mitochondria. Among the regulatory sequences that can be used, mention may be made, in a nonlimiting manner, of the signal sequences for expression of mitochondrial genes such as COX1 and COX2.

According to another advantageous embodiment of the method according to the invention, said mitochondrial transformation reporter gene is a gene encoding one of the proteins of the yeast respiratory chain [genes for apocytochrome b and for subunits I, II and III of cytochrome oxidase (COX)]; said gene corresponding to a functional transcription unit including the promoter, the coding sequence and the transcription terminator.

When a vector containing a mitochondrial transformation reporter gene is used, preferably a vector of bacterial origin (plasmid), for example the plasmid pUC18, only two RNAs are therefore produced in the system according to the invention: the RNA of the reporter gene (COX2) and the RNA of interest. It is therefore easy to separate these two RNAs by virtue of their respective sizes, for example by electrophoresis, HPLC, NMR, affinity, etc. In addition, this reporter gene allows complementation of a mit$^-$ allele of the reporter gene present in the transformation tester strain, either in trans (transcomplementation) or by homologous recombination.

According to another advantageous embodiment of the method according to the invention, said mitochondrial transformation vector contains a fragment of a mitochondrial transformation reporter gene as defined above. When the reporter gene (COX2) is replaced with a fragment of this same gene which is not transcribed, the purification of the RNA of interest is easier, given that said RNA of interest is the one and only RNA present in the mitochondria. In addition, this reporter gene fragment allows complementation by homologous recombination of a mit$^-$ allele of said reporter gene present in the transformation tester strain.

The mitochondrial transformation vector as defined above can also be improved in the following way: by introducing (i) sequences allowing greater stability of the gene of interest, for example by the addition of an Ori sequence (origin of replication of the mitochondrial DNA) of a yeast such as S. cerevisiae, so as to increase the efficiency of replication of the vector in the mitochondria, and/or (ii) sequences that facilitate purification of the RNA, as defined above, and optionally sequences for removing the RNA maturation sequences.

According to another advantageous embodiment of the method according to the invention, the transformation according to step (1) comprises the adsorption of said mitochondrial transcription vector onto metal microprojectiles (tungsten or gold) and the projection of said microprojectiles onto said cells, in a manner known per se, in accordance, for example, with the biolistic method as described in the article by N. Bonnefoy et al., (*Methods in Enzymology,* 2001, 350, 97-111). The device used is, for example, a PDS-1000/He system (BioRad). This instrument uses a helium shock wave to accelerate microscopic particles in the direction of a layer of cells on a Petri dish. The size of these particles is 0.45 µm in diameter, which represents approximately 10% of the diameter of a yeast cell. In a limited number of cells, these microprojectiles cross the yeast wall and reach the mitochondrion. Since the mitochondria of rho$^0$ cells do not contain any of their own DNA, the DNA introduced by biolistics is the only DNA present in these organelles and synthetic rho$^-$ cells are thus obtained.

According to another advantageous embodiment of the method according to the invention, the yeast cells lacking mitochondrial DNA are those of a rho$^0$ strain. By way of nonlimiting example, mention may be made of the following rho$^0$ strains derived from the DBY947 strain: ATCC 201440 (MCC109rho$^0$ [MATa, ade2-101, ura3-52, karl-1 (rho$^0$)]) ATCC 201442 (MCC123rho$^0$ [MATa, ade2-101, ura3-52, karl-1 (rho$^0$)]) and DFS160rho$^0$ (M. E. Sanchirico et al., EMBO J., 1998, 17, 19, 5796-5804. d; Steele et al., PNAS, 1996, 93, 5253-5257).

According to another advantageous embodiment of the method according to the invention, said yeast cells lacking mitochondrial DNA are modified such that the genes encoding RNA degradation proteins in the mitochondrion are inactivated (modified or deleted). Several mitochondrial proteins, all of nuclear origin, that are involved in the turnover of mitochondrial RNAs, for instance Suv3p and a subunit of a 3'-5' exoribonuclease (DSS1p) are known to date. By using yeast strains in which the genes of these proteins have been inactivated (ΔSUV3 or ΔDSS1 strains), such as in particular the ΔSUV3Δi and ΔDSSΔi strains (Dziembowski et al., J. Biol. Chem., 2003, 278, 1603-1611) or the ATCC strains Nos. 4002799, 4012799, 4022799 and 4032799, it is possible to increase the stability of the RNAs synthesized in the mitochondrion, according to the method of the invention.

According to another advantageous embodiment of the method according to the invention, said yeast cells lacking mitochondrial DNA comprise a copy of a gene encoding an exogenous RNA polymerase and including a mitochondrial targeting sequence, integrated into their chromosome (chromosomal copy).

The exogenous RNA polymerase sequences that are functional in yeast cells and the mitochondrial targeting sequences are known; they are introduced into the yeast chromosome by homologous recombination, according to conventional techniques known to those skilled in the art.

The majority of mitochondrial proteins are of nuclear origin. This is in particular the case for the protein machinery necessary for the transcription of DNA to RNA. This machinery is therefore imported into the mitochondrion and remains functional even when the cells are rho$^0$ and therefore lacking mitochondrial DNA. On the other hand, part of the machinery for the translation of RNA to protein is encoded by the mitochondrial genome. Consequently, if the mitochondrial genome is absent—this is the case in the synthetic rho$^-$ cells, the foreign DNA introduced into the mitochondrion is not translated to protein. In this context, the DNA introduced by biolistics is the only DNA present in the mitochondria of the synthetic rho$^-$ cells obtained. It will be transcribed to RNA, but this RNA will not be translated to protein.

According to another advantageous embodiment of said method, step (1) comprises cotransforming the yeast with said mitochondrial transcription vector and a vector that is replicative in yeast, comprising a nuclear selection marker, for instance an auxotrophic marker for the transformed cells, such as LEU2; said vector is, for example, pFL46L (ATCC No. 77210) or Yep351 (ATCC No. 37672) (FIG. 3). The wild-type gene carried by the plasmid thus functionally complements the mutated gene carried by the transformed cells.

According to another advantageous embodiment of the method according to the invention, step (2) comprises:

($a_0$) crossing the synthetic rho⁻ transformed yeast, obtained at the end of step (1), with a yeast tester strain of rho⁺ mit⁻ type, so as to facilitate the identification of said transformed cells, said tester strain containing a local alteration (nucleotide substitution (point mutation), short deletion or insertion) in a region of the mitochondrial genome corresponding to the mitochondrial transformation reporter gene or to the fragment of this gene used in step (1), for example one of the genes of the yeast respiratory chain, such as COX2; the corresponding wild-type sequence (gene or gene fragment) is carried by the mitochondrial transcription vector used to transform the mitochondrion of the rho⁰ host strain in step (1), ($b_0$) identifying the mitochondrial transformants (synthetic rho⁻ cells) that, once crossed, give diploid cells capable of growing on a non-fermentable medium: only the cells of the host strain that contain, in their mitochondria, the mitochondrial transcription vector carrying the gene of interest and the wild-type allele of the mit⁻ mutation present in the mitochondrial DNA of the tester strain will give, after recombination of the parental mitochondrial DNAs, rho⁺ mit⁺ recombinant diploid cells which will be revealed by their ability to grow on a non-fermentable medium (respiratory medium), after replica-plating of the diploids on velvet, on such a medium. On this medium, for example, when the mitochondrial transcription vector contains a reporter gene fragment, neither the parents of the cross (rho⁰ host strain and rho⁺ mit⁻ tester strain), nor the rho⁺ mit⁻ nonrecombinant diploids derived from this cross, will be capable of growing. This step makes it possible to define, on the initial dish obtained after bombardment of the rho⁰ host strain, areas where there are cells of this host strain in which the mitochondria have acquired the mitochondrial transcription vector carrying the gene of interest, and ($c_0$) repeating said crossing until isolated yeast colonies identified as being mitochondrial transformants carrying the mitochondrial transformation vector (synthetic rho⁻ cells) are obtained.

More specifically, the nuclear transformants obtained after bombardment are crossed with a strain which itself has a rho⁺ mitochondrial DNA but also a mit⁻ mutation which prevents it from growing on a respiratory medium; the corresponding wild-type sequence is present in the reporter gene or the reporter gene fragment carried by the mitochondrial transcription vector included in the synthetic rho⁻. In this way, after crossing, the mutated mitochondrial DNA and the corresponding wild-type sequence on the synthetic rho⁻ will be present together. Homologous recombination will then make it possible to correct the mit⁻ mutation, and the diploids obtained will again possess respiratory growth, hence the term "marker rescue". In practice: there are considered to be 1000 to 10 000 nuclear transformants distributed over the dish after bombardment, among which it is intended to identify those which are also mitochondrial transformants. This dish is therefore replica-plated on velvet (to keep the same arrangement of the clones on the Petri dish) on a dish of the same medium (stock dish) and on a layer of the rho⁺ mit⁻ tester strain. After crossing, the latter is replica-plated on a respiratory medium in order to pinpoint the clones which have allowed the marker rescue. By then going back to the stock dish (not crossed, replica of the original dish), the corresponding haploid synthetic rho⁻ clones are recovered since these are the ones that are ultimately selected (FIG. 3).

In other words, the two strains that are crossed in step ($a_0$) cannot grow on a non-fermentable medium. It will therefore be easy to pinpoint the recombinant clones that have recovered the ability to grow on this type of medium. It is not therefore necessary to select the diploids on a specific medium (specific in terms of auxotrophic markers) before replica-plating the crosses on a non-fermentable medium. Only the cells of the host strain that contain, in their mitochondria, the mitochondrial transcription vector will be able to give, after crossing, clones that can grow on a non-fermentable medium.

Several cases are possible: recombinant diploids, but also nonrecombinant diploids if the marker gene is whole in the vector (trans-complementation by the RNA produced by the DNA of the synthetic rho⁻), and, finally, recombinant or non-recombinant cytoductants (the kar 1-1 mutation of one of the two strains delays fusion of the nuclei and makes it possible to obtain, after crossing, haploids which have nevertheless undergone fusion of the cytoplasms and therefore of the mitochondria).

In step ($c_0$), the purification of the mitochondrial transformants is carried out by taking from the stock dish (not crossed) the area in which a clone has been pinpointed which gives, after crossing, growth on a non-fermentable medium, and repeating the crossing after re-plating of the cells as individual colonies; this step ($c_0$) therefore makes it possible to select, at the second or third round, a colony of a pure mitochondrial transformant. In fact, the problem is that, among 5000 clones on a single dish, it is not possible to be sure to have recovered a pure clone, but only a mixed area from which it is preferable to purify the synthetic rho⁻. For this, the recovered area is plated as individual colonies and the same tester cross is re-performed. After approximately 3 successive purifications, a pure synthetic rho⁻ clone was obtained.

As a variant, step (2) comprises:

($a_1$) a first selection or preselection of the yeast cells by means of the nuclear marker as defined above, by culturing in an appropriate medium, ($b_1$) a second selection from the yeast cells selected in ($a_1$), in accordance with steps ($a_0$), ($b_0$) and ($c_0$), as defined above.

For example, once the rho⁰ cells have been bombarded, they are incubated at 28° C., the optimal temperature for yeast growth. Firstly, the cells are incubated on a selected medium lacking the amino acid or the nucleotide corresponding to the auxotrophic marker of said cells. This mutation makes the growth of said cells dependent on the addition to the culture medium, for example, of the amino acid that can no longer be synthesized. To identify the mitochondrial transformants, the yeast capable of growing on selected medium are crossed with a strain having an opposite sex sign. This strain is mit⁻, its mitochondrial DNA is present, but the COX2 gene has been deleted. The diploids are selected on a medium with a non-fermentable carbon source. Only the yeast in which the mitochondria have been transformed with the plasmid carrying COX2 can form viable diploids with the strain mit⁻ COX2- on this type of medium (complementation by DNA recombination or trans-complementation by the COX2 "wild-type" RNA in the synthetic rho–). This cross is then repeated until isolated colonies identified as being mitochondrial transformants capable of producing the RNA of interest in their mitochondria are obtained (FIG. 3).

Preferably, and in accordance with the invention, after crossing with a strain carrying a mit⁻ mutation, for example in the COX2 gene, the complementation of this mutation can take place transiently in trans by translation of the messenger RNA of the wild-type gene (COX2) provided by the synthetic rho⁻ strain, after fusion of the parental mitochondrial networks. This crossing constitutes a test for identifying and selecting the transformants of interest with a view to producing the RNA of interest.

In other words, after the bombardment of the rho⁰ cells, the nuclear transformants are first of all preferably selected. There is a large number of them (5000 per Petri dish), such that the colonies which they produce are not well separated from one another. Therefore, in a first step, the crosses with the tester strain (by replica-plating on velvet) will make it possible to define, on the original shot dish, regions containing mitochondrial transformants (in general about ten per dish). The cells of this area will be diluted and re-plated on a solid medium, so as this time to obtain well-separated colonies. These individual colonies are again tested by crossing with the mit⁻ tester strain so as to identify those derived from cells containing, in their mitochondria, the DNA of interest.

According to another embodiment of the method according to the invention, the isolation of the mitochondria, in accordance with step (4) of the method according to the invention, advantageously comprises, after lysis or grinding of said cells, isolation of the mitochondria according to known methods, in particular on a sucrose gradient or according to the method described in Guérin B. et al., *Methods Enzymol.*, 1979, 55, 149-59.

Preferably, step (4) of the method according to the invention advantageously comprises, after lysis or grinding of said cells, isolation of the mitochondria by means of at least two appropriate centrifugation steps, preferably at speeds of between 750 g and 12 500 g, and recovery of the final centrifugation pellet.

In accordance with the invention, the purification of the mitochondrial RNA according to step (5) is carried out by conventional techniques. It can be carried out according to the protocol described in di Rago J P. et al., *J. Biol. Chem.*, 1988, 263, 12564-12570 or a modified protocol in which the step consisting of extraction and purification of the RNA of interest by means of successive phenolic extractions is replaced with a step consisting of purification of the RNA by adsorption on an appropriate resin, followed by detachment of the RNA in an appropriate solution, in particular in water.

According to another embodiment of the method according to the invention, the purification of the RNA according to step (5) comprises:
- eliminating the contaminating nucleic acids, in particular numerous RNAs attached at the periphery of the mitochondrion, in the presence of appropriate buffers, the first buffer comprising at least one divalent ion-chelating agent such as EDTA and EGTA, and the second buffer comprising an RNase and, optionally, a DNase,
- lysing the mitochondria, in the presence of at least one detergent, and a divalent ion-chelating agent, and within a pH range of between 7 and 8; by way of example, mention may be made of the following buffer: 1% SDS, 10 mM EDTA and Tris/HCl, pH 7.5; and
- isolating and purifying the RNA of interest by any appropriate means.

The RNA thus purified in an aqueous solution is assayed, analyzed on an agarose gel and sequenced.

Said RNA can be used as it is or can be subjected to additional modification steps according to the use envisioned. Among these modifications, which are carried out according to conventional techniques, mention may be made, in a non-limiting manner, of: cleavage of the maturation sequences; chemical modifications, in particular to increase the stability of the RNA in vivo, double-stranded hybridization, in particular so as to form an siRNA, digestion so as to obtain small fragments covering the entire gene.

A subject of the present invention is also a yeast strain lacking mitochondrial DNA, comprising a chromosomal copy of a gene encoding an exogenous RNA polymerase and including a mitochondrial targeting sequence. Preferably, said strain is obtained from rho⁰ and/or ΔSUV3 or ΔDSS1 cells, as defined above.

A subject of the present invention is also a yeast mitochondrial transformant lacking mitochondrial DNA as defined above. Preferably, said transformant is obtained from a strain that is rho⁰ and/or ΔSUV3 or ΔDSS1, and/or comprising an exogenous RNA polymerase, as defined above.

A subject of the present invention is also the use of mitochondrial transformants of yeast cells lacking mitochondrial DNA as defined above, for the industrial production of a heterologous RNA of interest.

A subject of the present invention is also a system for carrying out the industrial production of preselected heterologous RNA of interest, characterized in that it comprises:
- yeast cells transformed at least with a mitochondrial transcription vector (synthetic rho⁻ cells) comprising the DNA encoding the heterologous RNA of interest under the control of regulatory element(s) for mitochondrial transcription, and a mitochondrial transformation reporter gene or a fragment of said reporter gene,
- at least one suitable culture medium for selecting said transformed cells (mitochondrial transformants),
- tester yeast cells of rho⁺ mit⁻ type,
- appropriate fermenters and culture media, and
- appropriate buffers for isolating the mitochondria from the synthetic rho⁻ cells and extracting the RNA of interest therefrom.

Besides the above arrangements, the invention also comprises other arrangements that will emerge from the description which follows, which refers to examples of implementation of the method that is the subject of the present invention and also to the attached drawings in which.

It should be clearly understood, however, that these examples are given only by way of illustration of the subject of the invention, of which they in no way constitute a limitation.

EXAMPLE

Production of the RNA of the RIP1 Gene According to the Method of the Invention

A) Materials and Methods
1) Mitochondrial Transcription Vector pJM2 (pTZ18-U, with wild-type COX2; YIN J. et al., *Tsinghua Science and Technology*, 1999, 4, 2; Bio-Rad) into which the RIP1$^m$ gene has been cloned, mitochondrial-code version of the RIP1 gene encoding a subunit of respiratory chain complex III, flanked by the COX1 expression signal sequences.

2) Shuttle Vector Comprising a Nuclear Selection Marker Yep352 (2 p, URA3) (ATCC No. 37673)
3) Transformation of Mitochondria of *S. cerevisiae* Cells Lacking Mitochondrial DNA, with the Vectors as Described in 1) and 2)

The rho$^0$ derivative of the W303-1B strain (Matα, ade2, trp1, his3, leu2, ura3), called W303-1B (ATCC No. 201238)/ A/50, is cotransformed with the vectors as defined in 1) and 2), according to the biolistic method described in the article by N. Bonnefoy et al., (*Methods in Enzymology*, 2001, 350, 97-111), using a PDS-1000/He biolistic device (BioRad).

4) Method for Identifying the Transformed Cells

Firstly, the nuclear transformants are selected on a synthetic medium lacking uracil. The mitochondrial transformants are identified among the URA3$^+$ nuclear transformants by virtue of their ability to produce diploids with growth on non-fermentable medium after crossing with the tester strain TF145 (MATα, ade2) (Speno H. et al., *J. Biol. Chem.*, 1995, 270, 43, 25363-25369). This strain is incapable of growing on a non-fermentable medium (respiratory medium) because it comprises a deletion in the mitochondrial gene COX2 (cox2-17).

5) Yeast Cell Culture Conditions:

The mitochondrial transformants are cultured in fermenters until an exponential growth phase medium is obtained, in a rich medium containing galactose as carbon source.

6) Method for Purifying the Mitochondria and the RNA:
6.1) Isolation of Mitochondria The yeast mitochondrial transformants are cultured in a fermenter until an exponential growth phase medium is obtained, i.e. an OD of between 3 and 4. They are then harvested and lysed or ground and their mitochondria are purified by conventional methods.

Briefly, the protocol used is as follows:

The mitochondria of the mitochondrial transformants are isolated and purified after digestion of their cell wall with zymolyase in a medium (1.35 M sorbitol) that osmotically protects the integrity of the cells that have had their wall removed (called spheroplasts). The spheroplasts are subjected to an osmotic shock in a buffer that preserves the integrity of the mitochondria (0.6 M sorbitol). The cell debris (nuclei, walls) are removed by several (a minimum of 2) low-speed (750 g) centrifugations of the spheroplast lysate. The final supernatant is centrifuged at high speed (12 500 g) so as to pellet the mitochondria.

More specifically, the conditions are as follows:

I/Harvesting of Yeast

The yeast are centrifuged at low speed (4° C., 10 minutes at 3800 g).

II/2 Washing of the Yeast with Ice-Cold Distilled Water

The pellets are then taken up in chilled distilled water (4° C.).

Centrifugation is carried out at 4° C. for 5 min at 3800 g. The supernatant is removed and washing is carried out a second time with distilled water, followed by a further centrifugation under the same conditions.

III/Weakening of the Cell Wall

2-Mercaptoethanol breaks the disulfide bridges between the various mannoproteins of the wall, facilitating the subsequent action of the zymolyase. Based on the OD at 600 nm of the culture, the dry weight of yeast is evaluated by means of the following formula:

$$DW(g) = 0.28 \; OD \; \text{volume\_culture} \; (L)$$

Incubation is carried out in a volume of 20 ml of buffer/g of DW.

The pellet is therefore taken up in a pre-incubation buffer "SH" (0.5 M 2-mercaptoethanol, 0.1 M Tris-Base, pH 9.3) and is incubated for 10 min at 30° C. with agitation.

IV/Washing of the Yeast with the KCl Washing Buffer

The aim of these washes is to remove all traces of reducing agent.

The KCl buffer (0.5 M KCl, 10 mM Tris-Base, pH 7.0) is added to the SH preincubation buffer. Centrifugation is carried out at 4° C. for 5 min at 3800 g. The supernatant is removed. Two successive washes with the KCl buffer are thus carried out.

V/Digestion of the Cell Wall with Zymolyase at 30° C.

Zymolyase destroys the cell wall.

The yeast wall consists of a chitin backbone to which other proteins are added.

In order to digest the wall, one possibility is to use the zymolyase produced by the bacterium *Arthrobacter luteus* or an enzymatic mixture (cyto-helicase): snail (*Helix pomatia*) gastric juice enzyme, thereby giving yeast protoplasts.

The pellet is taken up with the digestion solution, in a proportion of 10 to 15 mg of zymolyase/10 ml of digestion buffer (1.35 M sorbitol, 1 mM EGTA, 10 mM citric acid, 30 mM disodium phosphate, pH 5.8).

The zymolyase digestion is stopped when 80 to 90% of the cells are digested, by making up the volume with the buffer for washing the protoplasts with KCl.

Centrifugation is then carried out for 5 min at 12 500 g.

VI/Washing of Protoplasts

The pellet is taken up rapidly in the washing buffer for protoplasts (or spheroplasts=cells from which the wall has been removed) (0.75 M sorbitol, 0.4 M mannitol, 0.1% BSA, 10 mM tris-maleate, pH 6.8). Centrifugation is carried out for 5 min at 12 500 g. The supernatant is removed and then the pellet is washed a second time.

VII/Homogenization and Grinding

The pellets are taken up in a few ml of the homogenization buffer (0.6 M mannitol, 2 mM EGTA, 0.2% BSA, 10 mM tris-maleate, pH 6.8). The preparation is poured into a potter-homogenizer. The potter homogenizer is moved up and down about ten times; the preparation is mixed at moderate speed, a maximum amount of the preparation is recovered, and the entire mixture is then redistributed into several tubes.

VIII/Isolation of Mitochondria by Differential Centrifugation

Low-speed (750 g) centrifugation is carried out for 8 min at 4° C. The supernatants are conserved. The pellet can optionally be taken up in the homogenization buffer and centrifuged and the supernatant added to the previous supernatant.

Centrifugation at higher speed (12 500 g) is carried out for 10 min at 4° C., and the supernatants are then removed.

The pellets are taken up in the recovery buffer (0.6 M mannitol, 2 mM EGTA, 10 mM tris-maleate, pH 6.8).

Low-speed centrifugation (8 min, 750 g at 4° C.) is carried out, followed by high-speed centrifugation of the supernatants (10 min, 12 500 g, at 4° C.). The supernatant is removed and a third low-speed/high-speed centrifugation cycle is optionally carried out.

IX/Final Recovery of Mitochondria

The mitochondrial pellet is taken up in a minimum volume of recovery buffer (mannitol, EGTA, tris-maleate, pH 6.8, as defined above), and then transferred into a potterhomogenizer in order to be homogenized.

X/Yield

Approximately 2-4 g of yeast are produced per 2 liters of culture.

A preparation of mitochondria with zymolyase makes it possible to obtain 1 to 1.5 ml of mitochondria at a concentration of 30 mg/ml of mitochondrial proteins, i.e. 30 to 45 mg of proteins.

6.2) RNA Extraction a) Method A

The mitochondria are, firstly, incubated in the presence of EDTA and of EGTA in order to remove from them the polysomes and the RNAs located at the periphery of the mitochondrion. They are then washed in buffer free of EDTA and of EGTA and incubated in this same buffer in the presence of RNase and of DNase in order to remove from them the cytoplasmic RNAs located at the periphery of the mitochondria and the remaining nuclear DNA. The action of the RNase and the DNase is interrupted by centrifugation at 12 500 g. The RNA of interest is then extracted according to the mitochondrial RNA extraction protocol described in Di Rago et al., 1988, mentioned above. The mitochondrial pellet is washed in buffer containing EDTA and EGTA, and lysed in the presence of 1% SDS, 10 mM EDTA and Tris HCl, pH 7.5. The nucleic acids are purified by successive phenolic extractions. The final aqueous phase is optionally washed by the action of chloroform::isoamyl acid, and the nucleic acids are then precipitated. In this step, the mitochondrial DNA is optionally degraded by adding DNase. The RNA thus purified is assayed, analyzed on an agarose gel and sequenced.

More specifically, the mitochondrial RNA extraction protocol is as follows:

10 mM EDTA was added to the recovery buffer (defined above); the various centrifugations are carried out at 4° C.
  Centrifugation at 12 500 g for 10 min.
  Recovery in recovery buffer, without EDTA or EGTA.
  Centrifugation at 12 500 g for 10 min.
  Pellet taken up in recovery buffer without EDTA or EGTA.
    Addition of RNase and of DNase and incubation at 37° C. for 15 min.
  Centrifugation at 12 500 g for 10 min.
  Washes in recovery buffer with EDTA and EGTA, followed by centrifugations.
  Pellet taken up in lysis buffer (2% SDS, 10 mM EDTA, 10 mM Tris HCl, pH 7.5) and addition of the same volume of 49:49:2 phenol:chloroform:isoamyl alcohol mixture. Mixture vortex for 3 min, left to stand for 2 min at 4° C., revortex for 2-3 min.
  Centrifugation for 5 min at 8 000 g and at 4° C.
  Removal of the aqueous phase and addition of the phenol/chloroform mixture, approximately 5 times.
  Addition to the final aqueous phase of 0.3 M of sodium acetate, pH 5.2, and 2.5 volumes of 100% ethanol. Mixture left to stand for 15 min at −80° C. and then centrifuged for 20 min at 8 000 g and at 4° C., and pellet washed.
  Pellet taken up in 3 ml of 10 mM $MgCl_2$, 20 mM Tris/acetate buffer, pH 7.4, containing 75 µl of 200 mM vanadyl-ribonucleoside complex (RNase inhibitor) and 2 µl of RNase-free DNase (in 50% glycerol at a concentration of 0.5 mg/ml).
  Removal of the DNase with one volume of 49:49:2 phenol/chloroform/isoamyl alcohol, and then one volume of 24:1 chloroform/isoamyl alcohol, and then one volume of water-saturated diethyl ether.
  Precipitation of the RNAs in the aqueous phase by addition of 0.3 M sodium acetate and 2.5 volumes of 100% ethanol.
  Pellet taken up in 50 to 100 µl of sterile water.
  Assaying and verification of the RNAs and then additional preparation and purification if necessary.

b) Method B

The mitochondria are firstly incubated in the presence of EDTA, of EGTA and of RNase in order to completely remove from the sample cytosolic RNAs normally attached to the outer periphery of the mitochondrial compartment. The extraction of the RNAs located inside the mitochondria is then carried out with an appropriate commercially available kit (Rneasy Protect Starter Kit™, QIAGEN, Cat. No. 74121). In this procedure, the mitochondrial sample is lysed with a specific buffer, immediately followed by purification of the RNAs that it contains in a single step by adsorption of the only RNAs of the sample onto an appropriate resin, followed by detachment of the RNAs with water. The RNA thus purified is assayed, analyzed on an agarose gel and sequenced.

B) Results

The purified mitochondrial RNAs are analyzed by the Northern blotting technique with a $P^{32}$-labeled DNA probe specific for the RIP1 gene and, as a control, a DNA probe specific for the endogenous mitochondrial gene COX1, also radiolabeled.

Figure 4:
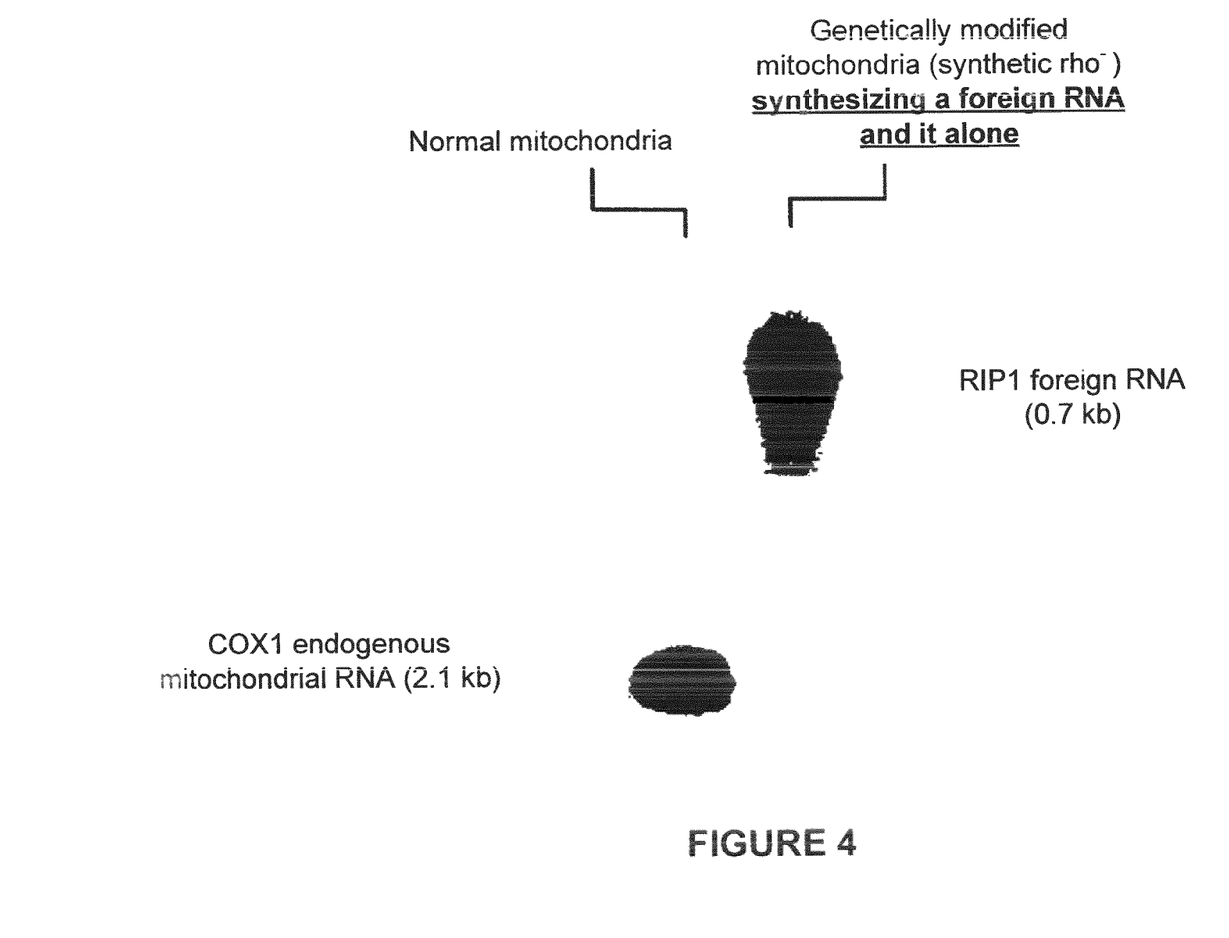
FIG. 4 illustrates the Northern blotting analysis of the mitochondrial RNA of synthetic rho⁻ yeast transformed with a mitochondrial transcription vector comprising the RIP1 gene.

The signal with the RIP1 probe and the absence of signal with the COX1 probe demonstrate that the mitochondria of the synthetic rho⁻ strain contain the RNA of interest, but no endogenous mitochondrial RNA (FIG. 4). By comparison, with the mitochondrial RNAs of a rho⁺ mit⁺ wild-type yeast strain, a signal is observed with the COX1 probe, but not with the RIP1 probe.

These results therefore demonstrate that the mitochondria of the synthetic rho⁻ strain are capable of specifically producing the RNA of interest.

As emerges from the above, the invention is in no way limited to those of its methods of implementation, execution and application that have just been more specifically described; on the contrary, it encompasses all the variants thereof that may occur to a person skilled in the art, without departing from the context or the scope of the present invention.

The invention claimed is:

1. A method for producing a heterologous RNA of interest, comprising:
  (1) transforming mitochondria of a yeast cell lacking mitochondrial DNA with a mitochondrial transcription vector that comprises at least one copy of the DNA encoding said heterologous RNA of interest under the control of regulatory element(s) for mitochondrial transcription, and a mitochondrial transformation reporter gene or a fragment of said reporter gene,
  (2) identifying a yeast mitochondrial transformant obtained in (1) which has mitochondria comprising the mitochondrial transcription vector but no mitochondrial DNA, wherein the only RNAs which are produced in said mitochondria by said mitochondrial transcription vector, are the heterologous RNA of interest alone, when the reporter gene or the fragment thereof are not transcribed, or the heterologous RNA of interest and the transcript of the reporter gene or reporter gene fragment, when said reporter gene or fragment thereof are transcribed;

(3) culturing the yeast mitochondrial transformant selected in (2), (4) isolating the mitochondria from the yeast mitochondrial transformant obtained in (3), and (5) extracting and purifying the heterologous RNA of interest from said mitochondria.

2. The method of claim 1, wherein said yeast cell lacking mitochondrial DNA is a rho$^0$ cell.

3. The method of claim 1, wherein said cell lacking mitochondrial DNA is obtained from a ΔSUI/3 strain.

4. The method of claim 1, wherein said DNA encoding the RNA of interest is under the control of a promoter and a transcription terminator that are functional in yeast mitochondria.

5. The method of claim 1, wherein said mitochondrial transformation reporter gene is a gene encoding one of the proteins of a yeast respiratory chain.

6. The method of claim 1, wherein said mitochondrial transcription vector comprises the sequence of an origin of replication of the mitochondrial DNA.

7. The method of claim 1, wherein the transformation according to (1) comprises the adsorption of said mitochondrial transcription vector onto metal microprojectiles and the projection of said microprojectiles onto said cells.

8. The method of claim 1, wherein (1) comprises the cotransformation of said yeast cells with said mitochondrial transcription vector and a vector that is replicative in yeast and that comprises a nuclear selection marker.

9. The method of claim 8, wherein said nuclear marker is an auxotrophic marker of said transformed cells.

10. The method of claim 1, wherein (2) comprises:
($a_0$) crossing the yeast mitochondrial transformant obtained in (1) with a yeast tester strain of rho$^+$ mit$^-$ type,
($b_0$) identifying a mitochondrial transformant which, once crossed, gives a diploid cell capable of growing on a non-fermentable medium, and
($c_0$) repeating said crossing until isolated yeast colonies identified as being mitochondrial transformants carrying the mitochondrial transformation vector are obtained.

11. The method of claim 1,
wherein (1) comprises cotransformation of said yeast cell with said mitochondrial transcription vector and a vector that is replicative in yeast and that comprises a nuclear selection marker, and wherein (2) comprises:
($a_1$) a first selection or preselection of the yeast cells by means of said nuclear marker, by culturing in an appropriate medium, and
($b_1$) a second selection from the yeast cell selected in ($a_1$), which comprises:
crossing the yeast mitochondrial transformant obtained, in (1) with a yeast tester strain of rho$^+$ mit$^-$ type,
identifying a mitochondrial transformant which, once crossed, gives a diploid cell capable of growing on a non-fermentable medium, and
repeating said crossing until isolated yeast colonies identified as being mitochondrial transformants carrying the mitochondrial transformation vector are obtained.

12. The method of claim 1, wherein the isolation of the mitochondria, in accordance with (4) of the method, comprises lysis or grinding of said cell, and then at least two centrifugation steps, and recovery of the final centrifugation pellet.

13. The method as claimed in claim 1, wherein (5) comprises:
eliminating the contaminating nucleic acids in the presence of appropriate buffers, the first buffer comprising at least one divalent ion-chelating agent, and the second buffer comprising an RNase and, optionally, a DNase,
lysing the mitochondria in the presence of at least one detergent and a divalent ion-chelating agent and within a pH range of between 7 and 8, and
isolating and purifying the RNA of interest.

14. A method for producing a heterologous RNA of interest comprising:
(1) transforming the mitochondria of a yeast cell lacking mitochondrial DNA with a mitochondrial transcription vector that comprises at least one copy of the DNA encoding said heterologous RNA of interest;
(2) identifying a yeast mitochondrial transformant obtained in (1) which has mitochondria comprising the mitochondrial transcription vector but no mitochondrial DNA, wherein the only RNAs which are produced in said mitochondria by said mitochondrial transcription vector are the heterologous RNA of interest, and the transcript of a mitochondrial transformation reporter gene or of a fragment of said reporter gene, only when said mitochondrial transcription vector comprises a mitochondrial transformation reporter gene or a fragment thereof that are transcribed;
(3) culturing the yeast mitochondrial transformant selected in (2);
(4) isolating the mitochondria from the yeast mitochondrial transformant obtained in (3), and
(5) extracting and purifying the heterologous RNA of interest from said mitochondria.

15. The method of claim 14, wherein the DNA encoding the heterologous RNA of interest is under the control of at least one regulatory element for mitochondrial transcription.

16. The method of claim 14, wherein said mitochondrial transcription vector comprises a mitochondrial transformation reporter gene.

17. A method for producing a heterologous RNA of interest, comprising:
(1) transforming the mitochondria of a yeast cell lacking mitochondrial DNA with a mitochondrial transcription vector that comprises at least one copy of the DNA encoding said heterologous RNA of interest;
(2) identifying a yeast mitochondrial transformant that has incorporated the DNA of interest;
(3) culturing the yeast mitochondrial transformant selected in 2);
(4) isolating the mitochondria from the yeast mitochondrial transformant obtained in 3), and
(5) extracting and purifying the heterologous RNA of interest from said mitochondria, wherein said mitochondrial transcription vector comprises a fragment of a mitochondrial transformation reporter gene that is not transcribed.

18. The method of claim 12 wherein the two centrifugation steps are performed at a speed between 750 g and 12,500 g.

* * * * *